(12) United States Patent
Besinger et al.

(10) Patent No.: US 8,349,399 B2
(45) Date of Patent: Jan. 8, 2013

(54) POWDER PARTICLES THAT ARE UNIFORMLY COATED WITH FUNCTIONAL GROUPS, METHOD FOR THEIR PRODUCTION AND USE THEREOF

(75) Inventors: Joern Besinger, Landshut (DE); Andreas Steinberg, Vilsheim (DE); Claudia Zimmerer, Altheim (DE)

(73) Assignee: Schott AG, Mainz (DE)

( * ) Notice: Subject to any disclaimer, the term of this patent is extended or adjusted under 35 U.S.C. 154(b) by 1139 days.

(21) Appl. No.: 11/578,770

(22) PCT Filed: May 4, 2005

(86) PCT No.: PCT/DE2005/000851
§ 371 (c)(1),
(2), (4) Date: Oct. 18, 2006

(87) PCT Pub. No.: WO2005/108320
PCT Pub. Date: Nov. 17, 2005

(65) Prior Publication Data
US 2007/0184185 A1 Aug. 9, 2007

(30) Foreign Application Priority Data
May 7, 2004 (DE) .................. 10 2004 022 566

(51) Int. Cl.
*B05D 7/00* (2006.01)
(52) U.S. Cl. ............................................... 427/212
(58) Field of Classification Search .......... 427/212, 427/215
See application file for complete search history.

(56) References Cited

U.S. PATENT DOCUMENTS

| 3,953,487 | A | | 4/1976 | Kratel et al. | |
|---|---|---|---|---|---|
| 4,407,984 | A | * | 10/1983 | Ratcliffe et al. | 522/14 |
| 4,544,359 | A | | 10/1985 | Waknine | |
| 5,057,151 | A | | 10/1991 | Schuster et al. | |
| 5,340,776 | A | | 8/1994 | Paschke et al. | |
| 5,501,732 | A | * | 3/1996 | Niedenzu et al. | 106/447 |
| 5,773,489 | A | | 6/1998 | Sato | |
| 6,010,085 | A | * | 1/2000 | Angeletakis | 241/21 |
| 6,010,776 | A | | 1/2000 | Exsted et al. | |

(Continued)

FOREIGN PATENT DOCUMENTS

DE  2 304 602  8/1974

(Continued)

OTHER PUBLICATIONS

Miyazaki et al. (JP 09-099246, machine translation).*

(Continued)

*Primary Examiner* — Michael Cleveland
*Assistant Examiner* — Robert Vetere
(74) *Attorney, Agent, or Firm* — Michael J. Striker

(57) ABSTRACT

The method produces powder particles that are uniformly coated with functional groups. It includes homogenizing, in an agitator mill, a suspension of glass, quartz, glass ceramic, and/or ceramic particles in a suspending agent together with a coating agent, so that the particles in the suspension react with the coating agent in the agitator mill to form the uniformly coated powder particles with functional groups. Preferably a weight ratio of the suspending agent to the particles is from 0.5:1 to 5:1. The suspending agent is preferably an aqueous solvent and the coating agent is preferably a silane. The uniformly coated powder particles have a particle size ($d_{50}$) of less than 2 µm, have a specific surface of 5 to 40 m²/g, and are free of agglomerates.

15 Claims, 3 Drawing Sheets

U.S. PATENT DOCUMENTS

| | | |
|---|---|---|
| 6,399,037 B1 | 6/2002 | Pflug et al. |
| 6,623,856 B1 * | 9/2003 | Kodas et al. ............ 428/402 |
| 2002/0193462 A1 | 12/2002 | Angeletakis et al. |

FOREIGN PATENT DOCUMENTS

| | | |
|---|---|---|
| DE | 23 44 388 | 3/1975 |
| DE | 38 39 900 | 5/1990 |
| DE | 41 00 604 | 2/1992 |
| EP | 0 363 070 | 4/1990 |
| EP | 1 316 589 | 6/2003 |
| GB | 2 251 814 | 7/1992 |
| JP | 58041810 | 3/1983 |
| JP | 06170868 | 6/1994 |
| JP | 07108156 | 4/1995 |
| JP | 8-104606 | 4/1996 |
| JP | 09099246 * | 4/1997 |
| JP | 2002-97388 | 4/2002 |
| JP | 2002538954 | 11/2002 |
| WO | 92/21632 | 12/1992 |
| WO | 00/54884 | 9/2000 |
| WO | 02/055028 | 7/2002 |

OTHER PUBLICATIONS

Miyazaki et al., JP 09-099246 (Machine Translation), Apr. 1997.*
Chemical Encyclopedia, p. 1142, Published on Apr. 1, 1994 by Tokyo Kagaku Dojin, Tokyo, Japan.
Plastic Encyclopedia, p. 761, Published on Oct. 20, 1994 by Kogyo Chosakai Publishing, Inc., Tokyo Japan.
Chemical Encyclopedia IV, p. 863, Published on Aug. 1, 1969 by Kyoritsushuppan Co., Ltd, Tokyo, Japan.

* cited by examiner

POWDER PARTICLES THAT ARE UNIFORMLY COATED WITH FUNCTIONAL GROUPS, METHOD FOR THEIR PRODUCTION AND USE THEREOF

CROSS-REFERENCE

This is the US National Stage of PCT/DE 2005/000851, filed on May 4, 2005, which claims priority of invention based on the disclosures in German Patent Application 10 2004 022 566.4, filed on May 7, 2004, in Germany. The aforesaid German Patent Application describes the same invention as disclosed and claimed herein below.

BACKGROUND OF THE INVENTION

The invention relates to a method for producing powder particles that are uniformly coated with functional groups and in particular glass powder, glass ceramic powder and/or ceramic powder.

Such powders find wide application in a large sector of technology and are obtained by coating a crude powder. For example, such powders in the form of glass powders are used in, among other fields, dental technology to prepare filled synthetic resins and in cosmetic and pharmaceutical formulations. They are also used both externally and internally in paints, lacquers, plasters and wood preservatives and as fillers in adhesives to increase their hardness or reduce their stretching properties. The preparation of, in particular, fine-particle powders with small or very small particle size is described, for example, in U.S. Pat. No. 6,010,085. Moreover, the preparation of very fine contaminant-free (high-purity) glass powders having a mean particle size $d_{50}$ of 0.2 μm to 10 μm is known from U.S. Pat. No. 5,340,776, the $d_{50}$ value of 0.2 μm meaning that 50% of all particles are smaller than 0.2 μm. By this method, a glass powder with a maximum particle size of $\leq 0.300$ μm is comminuted in an agitated ball mill or attritor mill with grinding elements consisting of glass the spallings of which do not affect the properties of the glass powder obtained, for example its refractive index. By this grinding method, the grinding is done in the presence of a grinding liquid until the desired particle size is attained. The grinding slurry is then frozen, and the grinding liquid is removed from the grinding slurry by freeze-drying.

If such powders are used as fillers for plastic materials employed in dental technology, it is important that the refractive index of the glass powder very closely match that of the plastic material so as to render the filled plastic material highly transparent and translucent. If the glass powder contains particles of contaminants such as spallings from the grinding mill that have a different refractive index, however, the translucency and transparency and possibly the color of the filled plastic material deteriorate so that often the powder can no longer be used or its use is severely restricted.

For this reason, as described in U.S. Pat. No. 6,010,085 and U.S. Pat. No. 5,340,776, all parts exposed to abrasion, such as the mill container and the grinding chamber and agitator are coated with the same material that constitutes the powder or with a plastic coating that can readily be removed by extraction, distillation or pyrolysis. When the glass particles are used as filler for plastic materials, the surface of the glass powder particles is usually/often coated with an appropriate silane to achieve better incorporation of the powder into the plastic matrix. Such a method is described, for example, in PCT/US92/04553. The silanization is accomplished by first dissolving the silane in an appropriate solvent and prehydrolyzing it and then applying it, for example in a mixer such as a planetary mixer or in a vibration or drum mill, onto the previously fully ground glass powder. During this procedure, however, the silanes also form dimers, trimers or even oligomers which not only form silanol agglomerates but because of the remaining silanol groups on the partly coated particles form aggregates with a size of up to 100-300 μm. With the aforesaid mixers or mills, the formation of these agglomerates or aggregates cannot be prevented. Even subsequent grinding of the agglomerates does not yield usable products.

SUMMARY OF THE INVENTION

Figure 1:
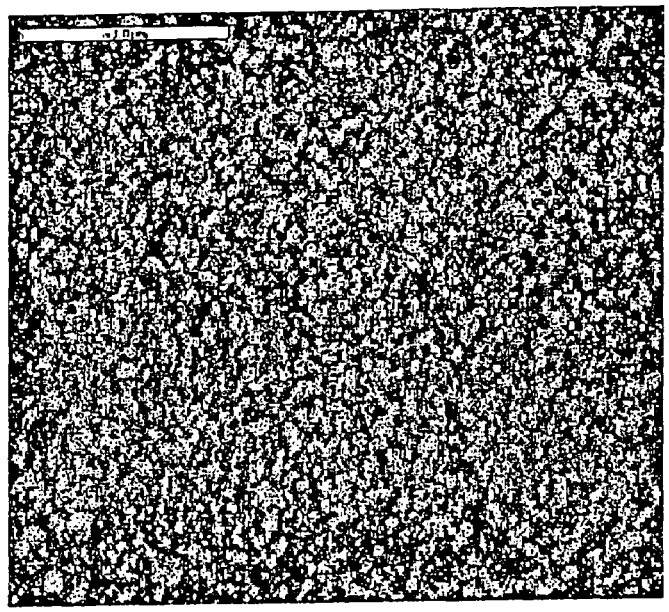
FIG. 1 is an electron micrograph of the powder obtained in Example 1.

The object of the invention is to provide a method whereby a powder can be uniformly coated with functional groups without forming agglomerates and without the powder particles being made to adhere to each other by the coating agent (so-called chemical agglomeration).

The invention also has for an object to increase the density of the coating attainable by prior-art methods.

This objective is attained by a method of producing coated powder particles that are uniformly coated with functional groups, said method comprising the step of homogenizing a suspension of crude particles in a suspending agent in an agitator mill together with a coating agent containing at least one functional group, so that the particles in the suspension react with the coating agent during the homogenizing to form the uniformly coated powder particles with the functional groups.

The objective is reached by the aforesaid method. In fact, this method provides high-purity, agglomerate-free and uniformly coated powders.

The method of the invention is preferably applied to a suspension of the powder in a suspending agent. In principle, the coating agent can also serve as the suspending agent. According to the invention, however, a liquid suspending agent is preferably used. The liquid suspending agent can be an inorganic or organic solvent, for example water or a hydrophilic, hydrophobic, protonic or aprotic organic solvent. Alcohols and ketones are preferred among the organic solvents. In principle, however, those skilled in the art will chose the suspending agent according to the powder and/or coating agent used.

The coating agents used according to the method of the invention contain at least one functional group capable of forming a chemical bond with the crude powder material and/or said agents firmly adhere adsorptively to the surface of the powder particle. Such groups depend on the powder material used. Preferably, however, silanol groups are used. Preferred silanols are alkoxysilanes, particularly trialkoxysilanes such as 3-triaminopropyltrimethoxysilane, 3-triaminopropyltriethoxysilane, 3-chloropropyltrimethoxysilane, 3-chloropropyltriethoxysilane, 2-aminoethyl-3-aminopropyltrimethoxysilane, 3-glycidyloxypropyltrimethoxysilane, 3-glycidyloxypropyltriethoxysilane, hexadecyltrimethoxysilane, isobutyltrimethoxysilane, isobutyltriethoxysilane, 3-mercaptopropyltrimethoxysilane, 3-methacryloxypropyltrimethoxysilane, 3-methacryloxypropyltriethoxysilane, methyltrimethoxysilane, methyltriethoxysilane, octyltrimethoxysilane, octyltriethoxysilane, pentyltrimethoxysilane, propyltrimethoxysilane, propyltriethoxysilane, (2-aminoethyl)-2-aminoethyl-3-aminopropyltrimethoxysilane, vinyltrimethoxysilane, vinyltriethoxysilane, tetramethoxysilane and tetraethoxysilane.

The coating agent preferably contains an additional functional group which after the coating step remains available for interaction or reaction with appropriate partners. Such functional groups are, for example, the amino, mercapto, acryl or methacryl, vinyl, substituted carboxyl groups, alkyl groups, particularly $C_1$- to $C_{20}$-alkyl groups, alkoxy groups, preferably $C_1$- to $C_{20}$-alkoxy groups, wherein the alkyl and the alkoxy groups can be straight-chain, branched, cyclic, heterocyclic and/or aromatic and possibly have double bonds, cyano groups, isocyano groups, cyanato groups, isocyanato groups, acid anhydrides, particularly cyclic anhydrides such as succinic anhydride, epoxy groups and particularly ethoxy groups such as glycidoxy groups, carbamates etc. Such reaction partners impart desirable properties to the powder surface, for example they facilitate incorporation into a plastic matrix, or they impart hydrophilic or hydrophobic properties, UV absorption, soil-repelling properties, improved suspendability etc.

The method of the invention can be applied to inorganic as well as organic powders or powder particles. Preferably, however, powder particles of an inorganic material are used. Particularly preferred powder materials are inorganic oxide materials such as $SiO_2$, $TiO_2$, glass, glass ceramic or glass ceramic-forming materials. The material can be crystalline or amorphous. Particularly preferred powder materials are glass, quartz, glass ceramic and ceramic. Preferred solvents and/or suspending agents are water or mixtures containing at least 50 wt. % of water and at least one water-soluble oxygen-containing organic compound with 1 to 5 carbon atoms in the molecule. Suitable organic compounds are aldehydes such as formaldehyde, acetaldehyde, propionaldehyde, butyraldehyde, pentanal, furthermore ketones such as acetone, methyl ethyl ketone, diethyl ketone, esters, for example ethyl acetate, methyl acetate, propyl acetate, methyl-, ethyl- or propyl formate or acids such as acetic acid and propionic acid. Monohydric, dihydric and trihydric alcohols are also well suited. A suitable trihydric alcohol is, for example, glycerol, and suitable dihydric alcohols are, for example, ethylene glycol or the propanediols. Particularly well suited are the monohydric alcohols, especially those with up to five carbon atoms in the molecule. Mixtures of water with organic compounds are preferred. Particularly preferred are acetone, tert.butyl alcohol, methanol, ethanol, n-propanol and i-propanol. Mixtures of these alcohols or acetone with 80 to 99 wt. % of water are unusually reactive and provide good homogenization.

The coating agent is preferably not added in the prereacted state. In particular, before its addition the agent is not presolvolyzed and especially not prehydrolyzed.

In the suspension used according to the invention, the weight ratio of solvent to powder particles is from 0.5:1 to 5:1 and particularly from 1:1 to 4:1. Particularly preferred weight ratios are in the range from 2:1 to 4:1, with 1.8:1 to 4:1 and particularly 1.9:1 to 3.5:1 being especially preferred.

The method of the invention preferably uses fine particles, sizes of $d_{50}$<5 μm and particularly of <2 μm being preferred. Particularly preferred are mean particle sizes $d_{50}$ of <0.4 μm and particularly <0.2 μm. The particles used for the method of the invention can be ground directly to the desired size in an attritor mill or they can be charged to said mill after they have previously been ground to the desired size. From appropriately fine starting powders, it is also possible to obtain with the attritor mill powders having a narrow particle size distributions of 50-400 nm and particularly of 180-220 nm.

According to a preferred embodiment of the invention, a coated attritor mill is used, as described, for example, in the afore-cited DE-A 41 00 604 or U.S. Pat. No. 6,010,085. A preferred coating material according to the invention is a polymerized resin. A preferred polymerized resin is polyurethane.

According to the invention, the coating agent is used in an amount from 0.5-15 wt. %, based on the weight of the powder. Preferred amounts are in the range of 1-12 wt. %, with 2-10 wt. % being particularly preferred. The optimum amount for a particular purpose also depends on the desired final fineness of the powder and can readily be determined by a person skilled in the art using simple tests.

At the end of the reaction, the suspension is removed from the attrition mill, and the suspending agent and unreacted coating agent are removed, preferably by drying. Useful drying methods have been found to be, in particular, the evaporation of the solvent or suspending agent by heating, optionally under vacuum. In many cases, freeze-drying is a preferred and also advantageous method.

According to the invention, in some cases it is preferred to subject the unreacted coating agent to extraction with a solvent that is appropriate for this purpose. Preferred solvents are those that solvatize the coating agent to be removed particularly well. In the case of trialkylsilanes, such solvents are, in particular, the alcohols. According to the method of the invention, impurities consisting of synthetic material that ended up in the reaction product as a result of spalling, for example resins and particularly polyurethanes, can also be removed by extraction, for example with an ether.

We have found that the method of the invention yields unusually fine and very pure coated powder particles. Moreover, it must be assumed that the coating obtained according to the invention is a monolayer. In addition, compared to prior-art methods, by means of the method of the invention, the amount of unbound silane can be dramatically reduced. The method of the invention affords unusually uniformly coated powder particles, because the formation of agglomerates or aggregates during the coating is prevented.

The invention also applies to coated powder materials themselves, and particularly to powder materials that are densely coated with a monolayer and have a particle size $d_{50}$ of <2 μm, particle sizes of <1.5 μm and particularly of <1 μm being particularly preferred. The powder is free of aggregates and agglomerates. Particularly preferred are powders with a particle size $d_{50}$ of <0.7 μm and <0.4 μm. Powders having a particle size of <0.2 μm are especially preferred. By $d_{50}$ is meant the mean particle diameter that characterizes the particle fineness obtained by making the powder pass through a screen. In other words, with a screen of a given mesh size, 50%, particularly wt. %, of the particles pass through the screen while the other 50% do not pass.

The method of the invention is carried out as follows.

In an agitator mill, the desired glass material that is to be coated is wet-ground to the desired size and then in this agitator mill treated with the coating agent either immediately thereafter or at any later point in time without prehydrolysis. The coating agent is first homogenized in the slurry and then, after the coating agent has been uniformly distributed in the glass powder slurry, it is gradually hydrolyzed.

The end of the silanization reaction is indicated by a marked increase in viscosity so that it may be assumed that the silanization reaction has gone to completion if the viscosity no longer changes or changes only to a minor extent.

After about 1 hour, the viscosity increases appreciably. The reaction has come to an end when the viscosity no longer changes (after approximately 30 more minutes). The slurry is pumped out and dried.

The silane content is determined from the weight loss caused by calcination of the organic residue.

The amount of silane that is not firmly bound is determined as follows. The powder is washed in isopropanol, after which the silane content is determined as described in the foregoing as weight loss caused by calcination of the organic residue.

The specific surface was determined by the BET method according to DIN [German Industry Standard] 66131 (1990) by use of a BET instrument of the Flow Sorb 2300 type supplied by the Micromeritics company. The gas used consisted of a 70:30 mixture of helium and nitrogen.

Depending on the final fineness to be attained, the pre-ground glass had a particle size $d_{50}$ in the range of 0.9-1.2 µm, 0.6-0.9 µm or 0.2-0.6 µm. The particle size distribution was determined with a Cilas 1064 L laser granulometer supplied by the Quantachrome company. The measurement was made on the ground slurry. The measurements were accurate to ±1 µm.

The invention also relates to the use of the particles obtained by the method of the invention as fillers, particularly in dental materials such as tooth prostheses or partial tooth prostheses, tooth fillings, in cosmetic and pharmaceutical formulations such as thickening agents and/or preservatives in ointments and pastes as well as lipsticks, in coatings and coverings, for example paints, lacquers, plasters and wood preservatives for both external and internal use, and particularly in UV-absorbing coatings or coatings used for protection from UV radiation, furthermore in adhesives, for example to increase their hardness or to reduce shrinkage and stretching and to prevent sedimentation.

The invention will be explained in greater detail by way of the following examples.

EXAMPLES

Example 1

According to the invention, 500 g of an ultrafine glass powder with a particle size $d_{50}$=0.7 µm was charged as an aqueous slurry to an agitator mill (types PML V+H, supplied by DRAIS GmbH, Germany). After sufficient homogenization of the slurry, 4 wt. % of methacryloxypropyltrimethoxysilane was slowly added to the slurry over a period of 3 to 5 minutes. After about 1 hour, the viscosity of the slurry increased appreciably. After an additional 30 min the silanization was complete and the slurry was pumped out. Drying of the slurry gave a silanized, agglomerate-free glass powder of high purity. The silane content determined from the calcination loss was 2.5%. The amount of unbound silane was 0%. The specific surface of the silanized powder was 20 m²/g. An electron micrograph of the powder thus obtained is shown in FIG. 1 (scaling: 10 µm).

Comparative Example 2

Figure 2:
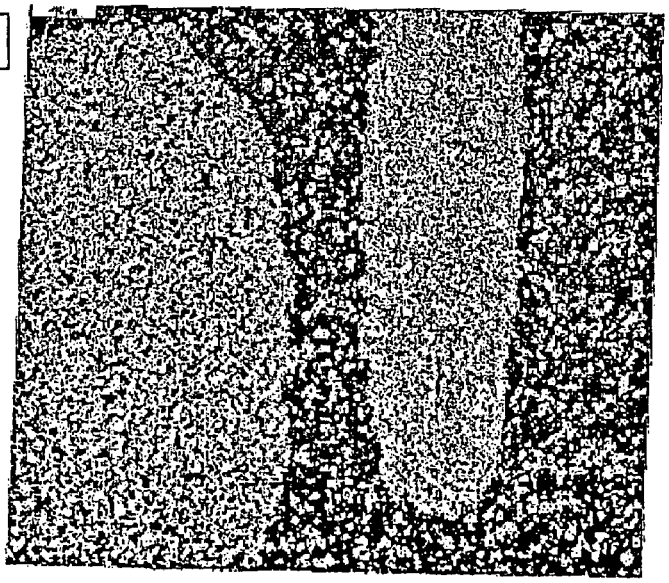
FIG. 2 is an electron micrograph of the powder obtained in Comparative Example 2.

In a mixing unit, 500 g of an ultrafine glass powder having a particle size $d_{50}$=0.7 µm was mixed with prehydrolyzed silane (4 wt. %). After a wetting period of about 2 hours, the mixture was discharged and dried. The silane content determined from the calcination loss was 1.8%. The amount of unbound silane was 22%. The specific surface of the silanized powder was 7 m²/g. An electron micrograph of the powder thus obtained is shown in FIG. 2 (scaling: 5 µm).

Example 3

Figure 3:
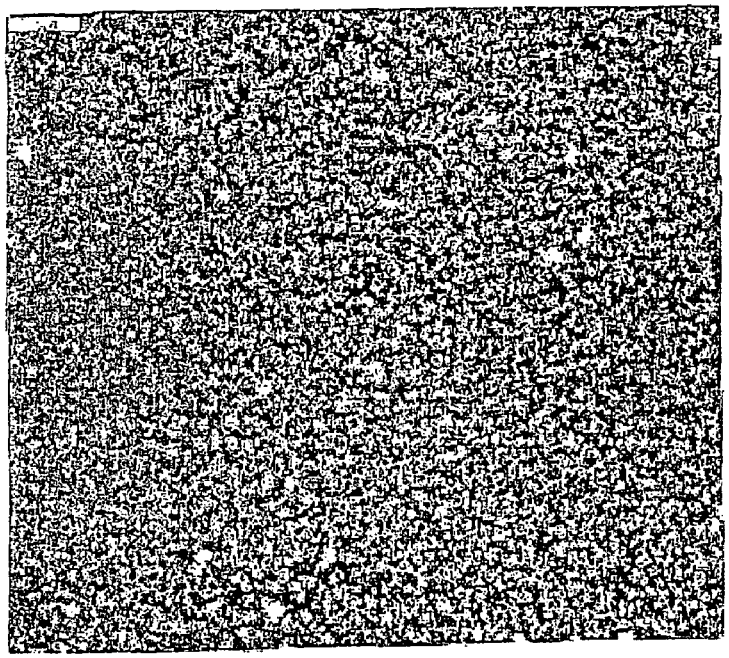
FIG. 3 is an electron micrograph of the powder obtained in Example 3.

According to the invention, 500 g of an ultrafine glass powder which had a particle size $d_{50}$=1.0 µm was charged as an aqueous slurry to an agitator agitated mill. After sufficient homogenization of the slurry, 3 wt. % of meth-acryloxypropyltrimethoxysilane was slowly added to the slurry. After about 1 hour, the viscosity of the slurry increased appreciably. After an additional 30 min the silanization was complete and the slurry was pumped out. Drying of the slurry gave a silanized, agglomerate-free glass powder of high purity. The silane content determined from the calcination loss was 1.9%. The amount of unbound silane was 0%. The specific surface of the silanized powder was 10 m²/g. An electron micrograph of the powder thus obtained is shown in FIG. 3 (scaling: 5 µm).

Comparative Example 4

Figure 4:
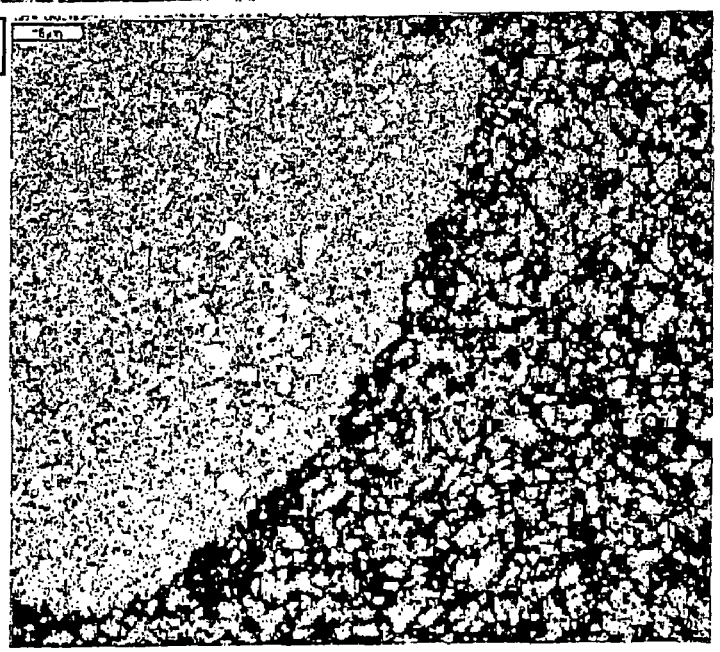
FIG. 4 is an electron micrograph of the powder obtained in Comparative Example 4.

In a mixing unit, 500 g of an ultrafine glass powder having a particle size $d_{50}$=1.0 µm was mixed with 3 wt. % of prehydrolyzed silane. After a wetting period of about 2 hours, the mixture was discharged and dried. The silane content determined from the calcination loss was 1.5%. The amount of unbound silane was 22%. The specific surface of the silanized powder was 3.2 m²/g. An electron micrograph of the powder thus obtained is shown in FIG. 4 (scaling: 5 µm).

Example 5

Figure 5:
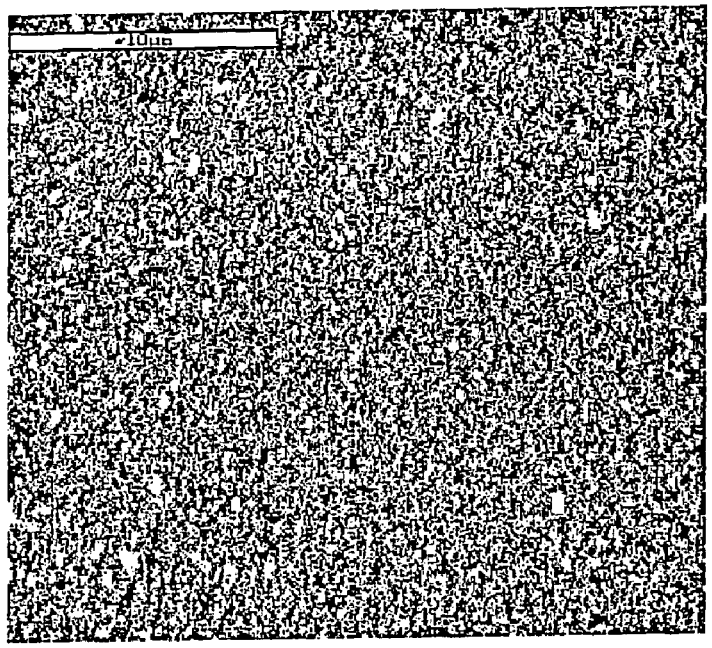
FIG. 5 is an electron micrograph of the powder obtained in Example 5.

According to the invention, in a laboratory agitator mill, 500 g of an ultrafine glass powder having a particle size $d_{50}$=0.4 µm was mixed with water to form a slurry which was then charged to the coating unit. After sufficient homogenization of the slurry, 9 wt. % of methacryloxypropyl-trimethoxysilane was slowly added to the slurry. After about 1 hour, the viscosity of the slurry increased appreciably. After an additional 30 min the silanization was complete and the slurry was pumped out. Drying of the slurry gave a silanized, agglomerate-free glass powder of high purity. The silane content determined from the calcination loss was 5%. The amount of unbound silane was 0%. The specific surface of the silanized powder was 40 m²/g. An electron micrograph of the powder thus obtained is shown in FIG. 5 (scaling: 10 µm).

Comparative Example 6

In a mixing unit, 500 g of an ultrafine glass powder having a particle size $d_{50}$=0.4 µm was mixed with prehydrolyzed silane (9 wt. %). After a wetting period of about 2 hours, the mixture was discharged and dried.

Figure 6:
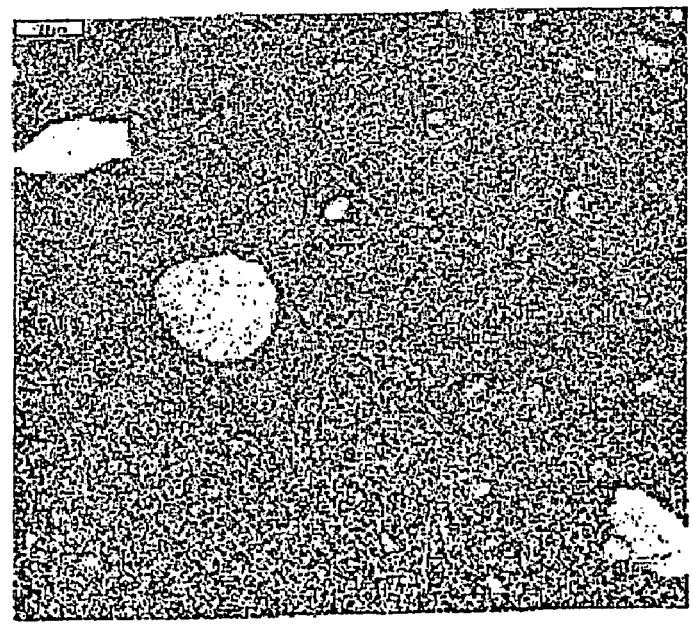
FIG. 6 is an electron micrograph of the powder obtained in Comparative Example 6.

The silane content determined from the calcination loss was 5%. The amount of unbound silane was 24.5%. The specific surface of the silanized powder was 10 m²/g. An electron micrograph of the powder thus obtained is shown in FIG. 6 (scaling: 20 µm).

The invention claimed is:
1. A method of producing coated powder particles that are uniformly coated with functional groups, said method consisting of the steps of:
   a) homogenizing, in an agitator mill, a suspension of glass particles, quartz particles, glass ceramic particles, and/ or ceramic particles in a suspending agent together with a functionalized silane and reacting, in the agitator mill, the particles with the functionalized silane during the homogenizing to form the uniformly coated powder particles without agglomerates; and b) when the reacting is finished, removing the suspension from the agitator mill and removing the uniformly coated powder particles from the suspending agent and from any unreacted silane that is present by a separation process, said separation process consisting of drying and optionally extracting with a solvent, so that the coated powder particles are obtained without any and all unbound silane and without said agglomerates;

wherein a weight ratio of the suspending agent to the particles is from 0.5:1 to 5:1;

wherein said suspending agent comprises water and/or at least one water-soluble oxygen-containing organic compound with 1 to 5 carbon atoms; and wherein said functionalized silane comprises at least one trialkoxysilane selected from the group consisting of 3-triaminopropyltrimethoxysilane, 3-triaminopropyltriethoxysilane, 3-chloropropyltrimethoxysilane, 3-chloropropyltriethoxysilane 2-aminoethyl-3-aminopropyltrimethoxysilane, 3-glycidyloxypropyltrimethoxysilane, 3-glycidyloxypropyltriethoxysilane, hexadecyltrimethoxysilane, iso-butyltrimethoxysilane, isobutyl-triethoxysilane, 3-mercaptopropyltrimethoxysilane, 3-methacryl-oxypropyltrimethoxysilane, 3-methacryloxypropyltriethoxysilane, methyltrimethoxy-silane, methyltriethoxysilane, octyltrimethoxy-silane, octyltriethoxysilane, pentyltrimethoxysilane, propyl-trimethoxysilane, propyltriethoxysilane, (2-aminoethyl)-2-aminoethyl-3-aminopropyltrimethoxysilane, vinyltrimethoxysilane, vinyl-triethoxysilane, tetramethoxysilane and tetraethoxysilane.

2. The method as defined in claim 1, wherein said functionalized silane is said 3-methacryloxypropyltrimethoxysilane or 3-methacryloxypropyltriethoxysilane.

3. The method as defined in claim 1, wherein said weight ratio of said suspending agent to said particles is from 2:1 to 4:1.

4. The method as defined in claim 1, wherein the agitator mill is a coated agitator mill.

5. The method as defined in claim 1, wherein a weight ratio of the particles to the functionalized silane is from 1:0.005 to 1:0.15.

6. The method as defined in claim 1, wherein said uniformly coated powder particles have a particle size ($d_{50}$) of less than 2 μm.

7. The method as defined in claim 1, wherein said uniformly coated powder particles have a specific surface of 5 to 40 $m^2/g$.

8. The method as defined in claim 1, wherein said separation process consists of said drying and said drying comprises heating, optionally under vacuum, or freeze-drying.

9. A uniformly coated powder obtainable by a method consisting of the steps of:
a) homogenizing, in an agitator mill, a suspension of glass particles, quartz particles, glass ceramic particles, and/or ceramic particles in a suspending agent together with a functionalized silane and reacting, in the agitator mill, the particles with the functionalized silane during the homogenizing to form the uniformly coated powder particles without agglomerates; and
b) when the reacting is finished, removing the suspension from the agitator mill and removing the uniformly coated powder particles from the suspending agent and from any unreacted silane that is present by a separation process, said separation process consisting of drying and optionally extracting with a solvent, so that the coated powder particles are obtained without any and all unbound silane and without said agglomerates;

wherein a weight ratio of the suspending agent to the particles is from 0.5:1 to 5:1;

wherein said suspending agent comprises water and/or at least one water-soluble oxygen-containing organic compound with 1 to 5 carbon atoms; and wherein said functionalized silane comprises at least one trialkoxysilane selected from the group consisting of 3-triaminopropyltrimethoxysilane, 3-triaminopropyltriethoxysilane, 3-chloropropyltrimethoxysilane, 3-chloropropyltriethoxysilane, 2-aminoethyl-3-aminopropyltrimethoxysilane, 3-glycidyloxypropyltrimethoxysilane, 3-glycidyloxypropyltriethoxysilane, hexadecyltrimethoxysilane, iso-butyltrimethoxysilane, isobutyl-triethoxysilane, 3-mercaptopropyltrimethoxysilane, 3-methacryl-oxypropyltrimethoxysilane, 3-methacryloxypropyltriethoxysilane, methyltrimethoxysilane, methyltriethoxysilane, octyltrimethoxy-silane, octyltriethoxysilane, pentyltrimethoxysilane, propyl-trimethoxysilane, propyltriethoxysilane, (2-aminoethyl)-2-aminoethyl-3-aminopropyltrimethoxysilane, vinyltrimethoxysilane, vinyl-triethoxysilane tetramethoxysilane and tetraethoxysilane.

10. The uniformly coated powder as defined in claim 9, in which said uniformly coated powder particles have a particle size ($d_{50}$) of less than 2 μm, have a specific surface of 5 to 40 $m^2/g$, and do not include said agglomerates.

11. The uniformly coated powder as defined in claim 9, wherein said separation process consists of said drying and said drying comprises heating, optionally under vacuum, or freeze-drying.

12. A filler in a dental material, a cosmetic preparation, a pharmaceutical preparation, a powder coating, a paint, a coating, a rubber mixture or an adhesive, wherein said filler consists of coated powder particles that are uniformly coated with functional groups and made by a method consisting of the steps of:
a) homogenizing, in an agitator mill, a suspension of glass particles, quartz particles, glass ceramic particles, and/or ceramic particles in a suspending agent together with a functionalized silane and reacting, in the agitator mill, the particles with the functionalized silane during the homogenizing to form the uniformly coated powder particles without agglomerates; and
b) when the reacting is finished, removing the suspension from the agitator mill and removing the uniformly coated powder particles from the suspending agent and from any unreacted silane that is present by a separation process, said separation process consisting of drying and optionally extracting with a solvent, so that the coated powder particles are obtained without any and all unbound silane and without said agglomerates;

wherein a weight ratio of the suspending agent to the particles is from 0.5:1 to 5:1;

wherein said suspending agent comprises water and/or at least one water-soluble oxygen-containing organic compound with 1 to 5 carbon atoms; and wherein said functionalized silane comprises at least one trialkoxysilane selected from the group consisting of 3-triaminopropyltrimethoxysilane, 3-triaminopropyltriethoxysilane, 3-chloropropyltrimethoxysilane, 3-chloropropyltriethoxysilane, 2-aminoethyl-3-aminopropyltrimethoxysilane, 3-glycidyloxypropyltrimethoxysilane, 3-glycidyloxypropyltriethoxysilane, hexadecyltrimethoxysilane iso-butyltrimethoxysilane, isobutyl-triethoxysilane, 3-mercaptopropyltrimethoxysilane, 3-methacryl-oxypropyltrimethoxysilane, 3-methacryloxypropyltriethoxysilane, methyltrimethoxysilane, methyltriethoxysilane, octyltrimethoxy-silane, octyltriethoxysilane, pentyltrimethoxysilane, propyl-trimethoxysilane, propyltriethoxysilane, (2-aminoethyl)-2-aminoethyl-3-aminopropyltrimethoxysilane, vinyltrimethoxysilane, vinyl-triethoxysilane, tetramethoxysilane and tetraethoxysilane.

13. The filler as defined in claim 12, wherein said uniformly coated powder particles have a particle size ($d_{50}$) of less than 2 μm, have a specific surface of 5 to 40 m$^2$/g, and do not include agglomerates.

14. The filler as defined in claim 12, wherein the suspending agent comprises water and the functionalized silane is said 3-methacryloxypropyltrimethoxysilane.

15. The filler as defined in claim 12, wherein said separation process consists of said drying and said drying comprises heating, optionally under vacuum, or freeze-drying.

* * * * *